United States Patent [19]
Günther

[11] Patent Number: 5,933,233
[45] Date of Patent: Aug. 3, 1999

[54] METHOD AND DEVICE FOR THE DETERMINATION OF MATERIAL-SPECIFIC PARAMETERS OF ONE OR A FEW MOLECULES BY MEANS OF CORRELATION SPECTROSCOPY

[75] Inventor: Rolf Günther, Hamburg, Germany

[73] Assignee: Evotec BioSystems GmbH, Hamburg, Germany

[21] Appl. No.: 08/836,032

[22] PCT Filed: Oct. 26, 1995

[86] PCT No.: PCT/EP95/04213

§ 371 Date: Apr. 28, 1997

§ 102(e) Date: Apr. 28, 1997

[87] PCT Pub. No.: WO96/13744

PCT Pub. Date: May 9, 1996

[30] Foreign Application Priority Data

Oct. 27, 1994 [DE] Germany ............... 44 38 391

[51] Int. Cl.⁶ ................................. G01N 21/64
[52] U.S. Cl. ................... 356/318; 250/458.1
[58] Field of Search ................ 356/300, 317, 356/318, 417; 250/458.1, 459.1, 461.1, 461.2; 385/14

[56] References Cited

U.S. PATENT DOCUMENTS 5,446,534  8/1995  Goldman ..................... 356/328

*Primary Examiner*—F. L. Evans
*Attorney, Agent, or Firm*—Jacobson, Price, Holman & Stern, PLLC

[57] ABSTRACT

A method for the determination of material-specific parameters of one or a few molecules by means of correlation spectroscopy wherein the molecule or molecules in a sample in which the molecule(s) to be determined is (are) present in relatively high concentrations is (are) excited by electromagnetic radiation (excitation radiation) to emit electromagnetic radiation (emission radiation) wherein said excitation and/or emission radiation passes a means which is permeable to the corresponding wavelength of said electromagnetic radiation which means is disposed between an excitation or emission radiation source and an excitation or emission radiation detector, said means for transmitting electromagnetic waves having at least one region the largest dimension of which in at least one direction of space is smaller than the wavelength of said excitation and/or emission radiation of said molecule or molecules.

23 Claims, 2 Drawing Sheets

METHOD AND DEVICE FOR THE DETERMINATION OF MATERIAL-SPECIFIC PARAMETERS OF ONE OR A FEW MOLECULES BY MEANS OF CORRELATION SPECTROSCOPY

The present invention pertains to a method for the determination of material-specific parameters of one or a few molecules by means of correlation spectroscopy, and a device for performing the method.

WO 94/16313 describes the method of fluorescence correlation spectroscopy (FCS) as an examination method. Due to a confocal arrangement, extremely small volume elements can be examined in a sample of quite different material compositions. Thus, by measuring the spectroscopical parameters of single or a few molecules, information can be achieved which permits conclusions on the material composition of such small volume elements to be drawn. However, this method requires relatively low concentrations of the molecules to be examined. If one desires to transfer the fluorescence correlation spectroscopy to systems in which relatively high concentrations of the molecule to be measured exist, the method reaches its limits since fluctuation analysis is no longer possible then. For example, if concentrations of more than 1 $\mu$m of the molecules to be examined are present in a measuring volume of $10^{-14}$ l, the fluorescence correlation spectroscopy employed so far is unsuitable.

From Fischer (J. Opt. Soc. Amb. B., Vol. 3, No. 10, pp. 1239–1244, October 1986), it is known that the concept of "surface-enhanced fluorescence spectroscopy" can be used to detect small changes in the optical properties of the microenvironment of a single small scattering object. Submicron apertures in thin silver or gold films coated on a microscope slide are used to analyze the properties of the solution to be examined.

Srivastava and Badyopadhyay (Rev. Sci. Instrum. 61 (2), 1990) describe a device for measuring the photoluminescence using optical fibers for guiding the excitation and emission radiations. This spectrometer is employed for determining photoluminescence spectra of several III–V components.

Miniaturized examination systems are described, e.g., in DD 271 953 A1. There is disclosed a means for the automated photometric analysis of minute sample quantities which can perform transmission (absorbance) and fluorescence measurements. Wave guide sheets which are in optical contact with at least one sample at their surface at least in sections thereof are implemented in a support. For each wave guide sheet, means implemented in the support are provided for coupling electromagnetic radiation into the wave guide sheets. For integration in peripheric technology, the support is fastened on a transport means which provides contact with means for the preparation and after-processing of the sample.

However, none of the methods described enables an extension of the measuring limits of correlation spectroscopy towards higher concentrations. In particular, no miniaturized device for performing correlation spectroscopy has been described previously. Such a device would be desirable in modern biotechnology, especially evolutive biotechnology.

Thus, it has been the object of the invention to develop a powerful examination system which enables the determination of material-specific parameters of molecules in relatively highly concentrated solutions by means of correlation spectroscopy, in particular fluorescence correlation spectroscopy. This examination system should be miniaturizable.

Surprisingly, the object of the invention is achieved by a method for the determination of material-specific parameters of one or a few molecules in a sample in which the molecule(s) to be determined is (are) present in relatively high concentrations wherein said molecule or molecules is (are) excited by electromagnetic radiation (excitation radiation) to emit electromagnetic radiation (emission radiation) wherein said excitation and/or emission radiation passes a means which is permeable to the corresponding wavelength of this electromagnetic radiation which means is disposed between an excitation or emission radiation source and an excitation or emission radiation detector, said means for transmitting electromagnetic waves having at least one region the largest dimension of which in at least one direction of space is smaller than the wavelength of said excitation and/or emission radiation of said molecule or molecules.

Figure 1:
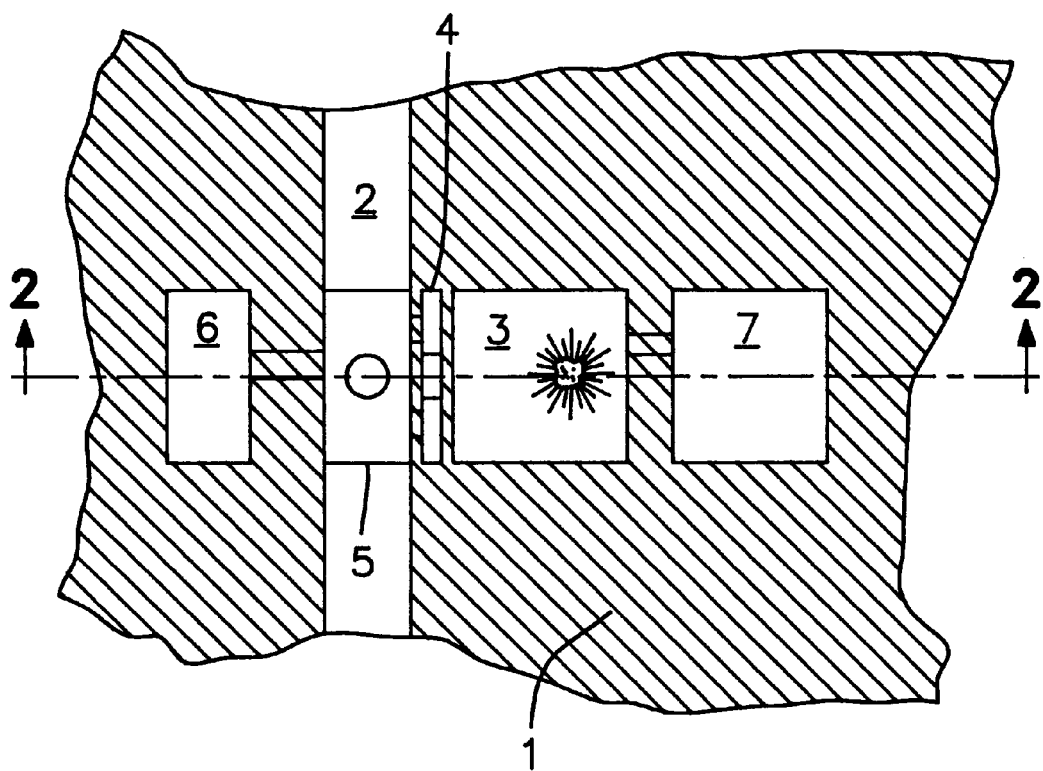
FIG. 1 is a schematic plan view of an embodiment for a device according to the invention.

The method according to the invention is based on the principle of optical near field microscopy. Normally, a beam of light cannot be focussed to a diameter which is substantially smaller than its wavelength. However, if it meets a correspondingly small aperture, the electromagnetic field penetrates through the aperture, but rapidly fades in further distance from the aperture.

The means permeable to electromagnetic radiation to be used according to the invention preferably has regions in the form of pinhole apertures or slit diaphragms. In particular, the means has regions which can be optically coupled with focussing optical elements, such as microlenses, gradient index lenses or binary optical elements, through optical waveguides and/or can be integrated into the optical waveguide.

Both the excitation light and the emitted light can be filtered by optical waveguides, especially in combination with focussing elements. In such a configuration, the emitted light, especially the fluorescent light, can be guided to a suitable detector either through the same glass fiber as the excitation light, provided with a beam splitter, or after being coupled into another optical waveguide.

A laser is preferably used as the light source. The light of this laser is focussed to a small volume element through an aperture or through the tapered end of a fiber the coat of which is coated to be optically impermeable. The sample is preferably measured in a flow-through capillary or in a stagnant solution (batch). Two-dimensional arrangements of such batches are preferably disposed in wafers as have been described in P 43 22 147.5. The sample compartment directly abuts on another slit or the tapered end of a second fiber which transmits the fluorescent light through an appropriate filter to the detector element. By using focussing elements, the quality of the light beam can be improved, and an arrangement can be realized which makes use of the same light path for both excitation and detection. Combinations with conventional FCS are also possible, e.g. excitation with the fiber described and detection through an ordinary microscope objective or vice versa.

The advantages of the method according to the invention are in particular:

a) higher concentrations can be measured;
b) the focus of a near field microscope is substantially smaller than that of a conventional microscope (about 50 to 100 nm vs.>300 nm). Thus, the diffusion times of the molecules through the measuring element become shorter, and correspondingly shorter measuring times become possible;
c) tapered fibers can be produced with less cost than microscope objectives;
d) depending on the diameter of the fiber end, several fibers may be grouped around the measuring volume in which the molecule or molecules to be measured is or are present, thus allowing excitation or detection at different wavelengths using one fiber per wavelength;
e) several fibers can be employed simultaneously in an arbitrary mutual arrangement in space;
f) the smaller focus results in a smaller influence of photo-bleaching of the dye molecules on the correlation function. This advantage is all the more relevant, the more slowly the observed particles diffuse.

Another object of the invention is to provide the examination system in a miniaturized design.

Laser and light emitting diodes (LDs and LEDs) used in optoelectronics are miniaturizable and thus can be appropriately used as light sources. The excitation radiation is preferably supplied by a unit which is a semiconductor laser or a frequency-multiplied semiconductor laser. In particular, devices are preferably employed which provide light pulses amplified by means of waveguides, such as glass fibers. These include, in particular, erbium-doped glass fibers. Thus, the light coupled out of the active layer is focussed to a small volume element through a miniaturized tapered optical waveguide. Optionally, pinhole apertures or aperture slits may be additionally employed. The detector is placed behind similar optics so that the focuses are superimposed (confocally). The angle at which the excitation and detector optics are arranged can be arbitrarily adjusted. It is particularly preferred to measure the emission radiation by a detector unit such as a pin layer connected as a photodiode, avalanche photodiodes or photomultipliers. In the X-ray region, Si:Li, Ge:Li detectors are employed.

By using all these elements, an FCS device can be assembled the components of which may be integrated on a chip and which can be manufactured with the usual microstructure production methods.

In addition to the light sources and detectors mentioned, refractive or diffractive optical elements may be used which effect light focussing in a similar way as lenses do. Thus, the device can be designed with both conventional and near field optics. The use of a microscope can be completely omitted.

For the micro-FCS variants, arrangements are possible with are similar to one another:

a) One or two detectors are disposed perpendicular to the incident fluorescent light.
b) In the transmission direction of the excitation light, an additional detector alternatively to the variant mentioned under a), or such a detector in a single arrangement, each in combination with a suitable filter.
c) A plurality of detectors arranged along a flow-through capillary. The detectors can be adjusted to exactly compensate the superimposed flow rate in the capillary. It is also possible in this variant to illuminate the whole capillary and to effect the limitation to the small space volume by the detector optics only.
d) A detector array which is arranged radially around the capillary to which the fluorescent light is supplied by means of optical waveguides. The fluorescent light can be coupled into the fibers by means of a microlense array.

The advantages of these variants are:

1. A significant reduction of the number of necessary components.
2. A parallel FCS unit can be readily assembled.
3. Due to the reduced dimensions, the FCS may be easily handled as a table-top device, optionally even as highly parallel equipment.
4. The detector arrangement according to c) enables the analysis of the change of fluorescence of a sample with time.
5. The radial detector array enables the miniaturization of cross-correlation when several light sources are used.
6. Highly reduced production costs in series production.
7. Integration of such a miniaturized FCS design in systems produced by microsystem technology (flow reactor, peptide parallel synthesis) can be realized.
8. Reduction of stray capacitance at amplifiers and control electronics by integration of such units directly on the chip. This involves a substantial increase in sensitivity of the measuring electronics.

As the electromagnetic radiation of emission and/or excitation, the method according to the invention preferably uses those having frequencies within the typical range of chemiluminescence, nuclear resonance fluorescence and X-ray fluorescence.

According to the invention, the interaction of chemiluminescence can also be measured via coupling with other physical effects, such as nuclear magnetic resonance, generally electric, magnetic and electromagnetic fields (spectral line splitting), frequency doubling (SHG), sum and difference frequency, vibration effects, coupling to phonons of the surrounding solid phase, for example, surface plasmons as emission radiation, or be combined with atomic force microscopy.

A preferred arrangement of FCS is the focussing the observed area to a small volume element in which single photons are counted and evaluated by means of correlation analysis. These photons must not necessarily be derived from the fluorescence of a molecule. Other sources may also serve this purpose. For example, the fluorescence quenching of a single molecule can be detected by electron spin resonance. In addition, further processes can be employed to yield photons. These may involve non-linear optical effects (frequency doubling or tripling (SHG or THG), sum and difference frequency). Although the energy densities required for an efficient yield are difficult to reach in continuous excitation and could also result in a rapid destruction of the dye, P 43 42 703 describes the use of a light source pulsed with a high frequency. In this way, the aforementioned problems can be avoided.

Another source of emission radiation is electrochemiluminescence. In this case, it is preferred to dispose an electrode near the observed volume.

The development of a suitable FCS device for utilizing inner levels permits a smaller focus due to the smaller wavelength used. Also, the fluorescence labeling of the species to be examined may in some cases become unnecessary. Conveniently, wavelengths within the so-called "water window" (between 284 and 543 eV) will be selected for excitation. In this wavelength region, water is transparent (no absorption by oxygen), while organic substances absorb through the carbon contained therein.

Preferably, a number of detectors are arranged in such a way that the molecule serving as the source of the emission radiation is observed, when passing the detectors, in a temporal correlation with this passing.

The method according to the invention can be performed, in particular, with a device which comprises an excitation radiation source disposed on a substrate, a means disposed in the beam path of the excitation and/or emission radiation which is permeable to the corresponding wavelength of this electromagnetic radiation, a detector for electromagnetic radiation, in particular caused by emission, and electronic circuit elements, optionally with evaluation units for the analysis of emitted electromagnetic radiation.

In a preferred embodiment, the substrate consists of a wafer made of a material used in microelectronics (such as Si, $SiO_2$, $Si_3N_4$, GaAs). The electronics required for controlling the laser and evaluating the measuring signal is integrated in the wafer as a monolith in this variant. In particular, the substrate may be a piezoelectric element.

The detector is preferably designed as a photodetector and disposed at the bottom of a channel traversing the substrate. The excitation radiation can in particular be irradiated at an angle of $>0$ and $\leq 180°$ with respect to the detector unit.

A preferred embodiment of the device according to the invention is characterized in that the detector unit is designed as a multidetector unit.

The process according to the invention for measuring the dwelling time of fluorescence-labeled molecules by illuminating and/or confocally imaging small volume elements can be realized through different devices. The device described in P 43 42 703 with elements of confocal laser spectroscopy is a preferred possibility.

However, the utilization of the device is limited technically:
  Only such objects can be analyzed which can be made available as a sample in the optical measuring device.
  The high manufacturing costs of the measuring device are a disadvantage.
  Due to its dimensions, the device is unhandy and is not much suited, e.g., for transportable equipment.
  Massive parallelization of measuring volumes is cumbersome.
  Expensive laser systems are used.
  Measuring volumes of >lambda are too large, e.g., for measuring at higher concentrations.

For circumventing the above mentioned drawback, the device according to the invention employs integrated optics with integrated laser light sources (laser diodes). This creates possibilities as provided by the devices and methods of near field microscopy.

Important aspects of fluorescence correlation spectroscopy (FCS) are
  the confocal arrangement of the excitation volume and the measuring volume, the volumes being as small as possible ($<<10^{-12}$ l).
  The evaluation of the light signal by correlation methods considering the diffusion times of translation and/or rotation of a molecule in the measuring volume.

To date, these requirements have been realized by a design using a confocal microscope. The use of miniaturized building elements or monolithic integration facilitate the measuring arrangement.

The miniaturized design according to the invention as manifested in the device according to the invention relates to a substrate in which excitation and detector unit are confocally integrated.

In a preferred embodiment, the substrate has a channel in the form of a capillary or a cleft in which the liquid to be examined is dispensed. It is analyzed there in a static condition or in continuous or discontinuous flow. Such an arrangement can typically be prepared with the known chemical or laser etching methods known from semiconductor technology, but also by means of the LIGA process. All materials compatible with the preparation technique can be used. Around the channel, excitation and detector unit are confocally arranged. The angle between the optical axes of excitation and detector unit can be arbitrary as long as the axes intersect in a common focus.

With the method according to the invention, very low concentrations ($<10^{-12}$ M) of fluorescing molecules can be determined. However, the method becomes cumbersome and less practicable when waiting for too many time units at unchanged space coordinates of one or more measuring volumes is required until a molecule to be measured happens to pass through the space element of the measuring volume. This problem is also important at higher concentrations ($>10^{-12}$ M) when the diffusion times are very short, as is the case, e.g., with cells and cell-bound molecules. In this case, the method can be performed in such a way according to the invention that the actual measuring process is preceeded by a scanning process in which the space coordinates are varied with time continuously or discontinuously until a signal of the desired quality is detected, e.g., the common appearance of a correlated fluorescence of two colors when the cross correlation method is used. Once a measuring signal has been detected, the measuring process is initiated according to the invention. The dwelling time of a scanning process can be less than one millisecond per measuring process for establishing that the single measuring volume or the measuring volumes measured in parallel include no molecule with the desired characteristics. In this approach, it has to be taken care that the average characteristic diffusion times are influenced in a calculatable way in their absolute values. This is achieved by the fact that, e.g., fixed molecules (e.g., on fixed bacterial cells) directly and exclusively reflect the variation of the change of space coordinates of the measuring volume with time, or with small mobile molecules and a discontinuous change of the space coordinates about half of the average dwelling time, since the molecules are already inside the measuring volume at the beginning of the measuring process.

Scanning processes which preceed the actual measurement are preferred in cases when cell populations are to be analyzed wherein only a fraction of the cells bear molecules or molecular complexes having the desired measuring properties. This is the case, for example, in the analysis of evolutively prepared mutant populations of recombinant cells, but also in the analysis of maternal blood for the presence of fetal nucleated erythrocytes which are to be analyzed for particular genes or chromosomal anomalies.

Other application examples are the functional genome analysis using phage or bacterial display systems, as well as corresponding applications in evolutive biotechnology. Both embodiments involve the detection and purposeful selection of cells or phages having specific binding properties to particular ligands before a background of non-reacting phages or bacteria.

Thus, the number of screened volume elements increases considerably. In combination with cross correlation, many volume elements can thus be screened in the $\mu$s to ns range in single and multi-array operation. The scanning motion is only interrupted when differently "colored" signals, e.g., can be detected in a correlated way in the volume element being observed. Then, the translational diffusion constant is determined. This time is statistically shortened by a calculatable time element (50%) as compared with the case that a particle must enter the volume element by itself or by forced diffusion. Once a particle has been detected, it can be detected once again by scanning the immediate environment.

The parallel illumination of several volume elements with confocal optics is known. The parallel illumination of measuring volumes with relative distances in the $\mu$m range cannot or only unsatisfactorily be achieved with the described devices. The illuminations desired according to the invention with dimensions in the lower $\mu$m range and smaller can be achieved according to the invention by using holographic grids. By using holographic grids or binary optical elements, extended arrays of small volume elements can be illuminated in parallel.

According to the invention, the measuring volumes are measured confocally for fluorescence properties of molecules contained therein, either by using several pinhole apertures in the object plane, by positioning multidetector elements in the object plane, or by using optical fiber bundles with the light being coupled thereinto in the object plane, and transmission to photon detectors.

In the highly parallelized illumination of small volume elements, the problem arises of recording the emitted fluorescence signals from the individual volume elements.

WO-A-94/16313 describes that it is possible to illuminate small space elements in parallel and image the respective fluorescence signals individually on multidetectors by using confocal pinhole aperture systems in the object plane, or to couple the signals into optical waveguides at the position of and instead of the pinhole apertures and guide them to detector elements, or to position the multidetectors themselves instead of and in the position of the pinhole apertures. There is also described the possibility to illuminate a larger volume element and combine it with the above described confocal parallel imaging of small subvolume elements.

However, in a high parallelization, the requirements for the number of detector arrays and the computational effort associated with the parallel processing of incoming data become considerable. According to the invention, these problems are solved by integrally acquiring the signals over several space elements in a further form of coupling small space elements illuminated in parallel with a recording device. This approach is useful, in particular, in such applications in which a great number of volume elements are to be screened the computational effort is to be minimized for the benefit of the computing capacity employed and the computing time the number of volume elements covered per measurement and thus the total measured volume is to be maximized signals of molecules, molecular complexes or cells are to be analyzed in high dilution the precision of the position-resolved detection is less important the number of emitted light quanta during the diffusion through a single space element is sufficient for a correlation.

FIG. 1 shows a schematic plan view of a preferred device for performing the method according to the invention as used when near field microscopy is employed.

Figure 2:
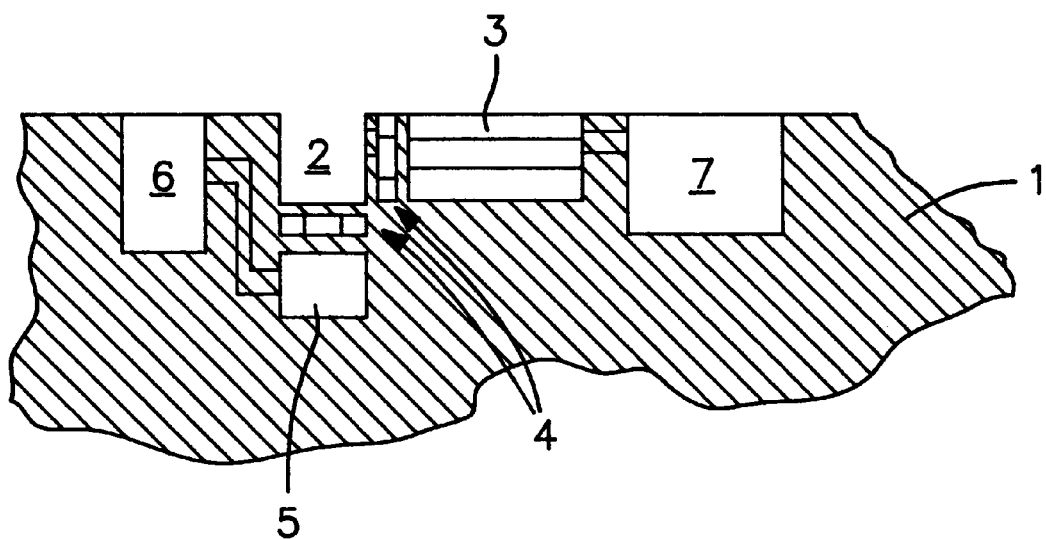
FIG. 2 is a cross-sectional view through the embodiment shown in FIG. 1.

FIG. 2 shows a cross-sectional view through the embodiment shown in FIG. 1 taken along the line II–II'. Into the substrate 1 which may be a silicon wafer, for example, a cavity is etched in the form of a capillary or channel 2. The laser diode 3 disposed on one side of the capillary or channel 2 is separated from the capillary or channel 2 by an aperture 4. A detector 5 which is also separated from the capillary or channel 2 by an aperture 4 is disposed below the capillary. Control units, such as the detector-controller 6 which in particular assumes the voltage supply of the detector, and the laser diode driver 7 are also integrated on the chip and and conductively connected with the units to be addressed. Preferably, the aperture 4 consists of a pinhole or a slit the size of which is smaller than the wavelength of the excitation radiation employed.

Figure 3:
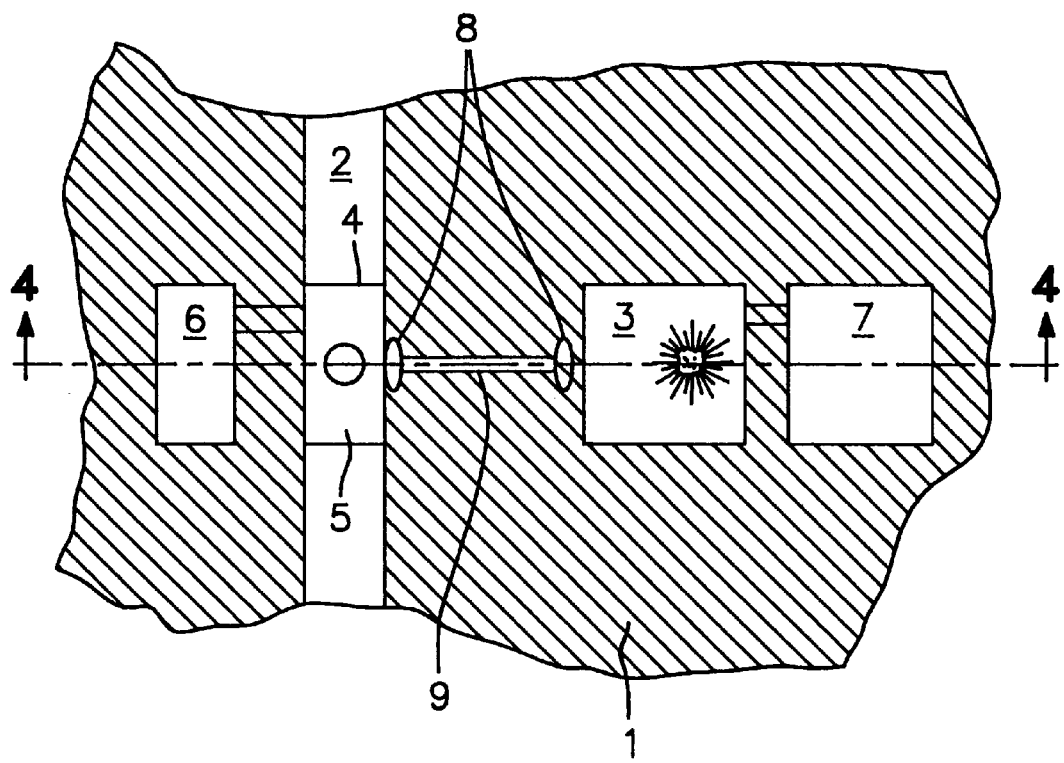
FIG. 3 is a schematic plan view of another embodiment of the device according to the invention.

FIG. 3 also shows a schematic plan view of another preferred device for performing the method according to the invention.

Figure 4:
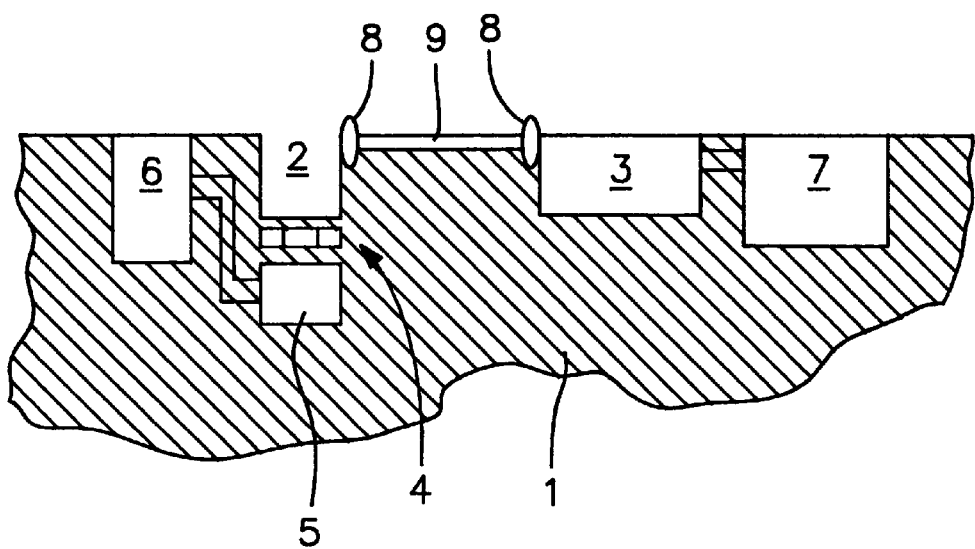
FIG. 4 is a cross-sectional view through the embodiment shown in FIG. 3

FIG. 4 shows a cross-sectional view through the configuration shown in FIG. 3 taken along the line IV–IV'. The light emitted from the laser diode 3 is coupled through a collimation optics 8 (microlens) into a waveguide 9 at the end of which there is a second microlens 8, for example. The latter produces the focus in the channel 2 which overlaps with the detection volume of detector 5 which is limited by the aperture 4.

I claim:

1. A method for the determination of material-specific parameters of one or a few molecules by means of correlation spectroscopy, characterized in that the molecule or molecules in a sample in which the molecule(s) to be determined is (are) present in relatively high concentrations is (are) excited by electromagnetic radiation (excitation radiation) to emit electromagnetic radiation (emission radiation) wherein said excitation and/or emission radiation passes a means which is permeable to the corresponding wavelength of said electromagnetic radiation which means is disposed in a beam path between an excitation or emission radiation source and an excitation or emission radiation detector, said means for transmitting electromagnetic waves having at least one region the largest dimension of which in at least one direction of space is smaller than the wavelength of said excitation and/or emission radiation of said molecule or molecules.

2. The method according to claim 1, characterized in that said means which is permeable to electromagnetic radiation has regions in the form of pinhole apertures or slit diaphragms.

3. The method according to claim 2, characterized in that said regions are optically coupled with focusing optical elements through optical waveguides and/or integrated into said optical waveguides.

4. The method according to claim 1, wherein the electromagnetic radiation of emission and/or excitation has frequencies within the typical range of luminescence, nuclear resonance fluorescence and X-ray fluorescence.

5. The method according to claim 1, wherein the interaction of luminescence is measured via coupling with other physical effects, coupling to phonons of the surrounding solid phase, or is combined with atomic force microscopy.

6. The method according to claim 1, wherein the excitation radiation is supplied by a unit which is a semiconductor laser or a frequency-multiplied semiconductor laser wherein light pulses produced by said unit are optionally amplified by means of waveguides.

7. The method according to claim 1, wherein the emission radiation is detected by a pin layer connected as a photodiode, avalanche photodiodes or photomultipliers.

8. The method according to claim 1, wherein the source of the radiation to be detected, the detector for the radiation, optics, and circuit elements are arranged on a substrate.

9. The method according to claim 1, wherein a number of detectors are arranged in such a way that the molecule serving as the source of the emission radiation is observed, when passing the detectors, in a temporal correlation with this passing.

10. The method according to claim 1, characterized in that electromaganetic radiation having energies between 284 and 543 eV is used for excitation.

11. The method according to claim 1, characterized in that the illumination of measuring volumes is effected by using holographic grids or binary optical elements.

12. The method according to claim 1, characterized in that the emission radiation of at least two measuring volumes is detected in an integrated way.

13. The method according to claim 3, characterized in that said focusing optical elements are microlenses, gradient index lenses, or binary optical elements.

14. The method according to claim 5, wherein the other physical effects are nuclear magnetic resonance, generally electric, magnetic or electromagnetic fields (spectral line splitting), frequency doubling (SHG,THG), sum or difference frequency, or vibration effects.

15. The method according to claim 6, wherein the waveguides are glass fibers.

16. A device for performing the method according to claim 1 comprising, integrated on a substrate (1), an arrangement of an electromagnetic excitation radiation source (3), a means for receiving a sample (2), a means (4) disposed in the beam path of the excitation and/or emission radiation which is permeable to the corresponding wavelength of this electromagnetic radiation, said means for transmitting electromagnetic waves having at least one region the largest dimension of which in at least one direction of space is smaller than the wavelength of said excitation and/or emission radiation, a detector (5) for electromagnetic radiation, and electronic circuit elements (6, 7), optionally with evaluation units for the analysis of emitted electromagnetic radiation.

17. The device according to claim 16, wherein said means which is permeable to electromagnetic radiation has regions in the form of pinhole apertures or slit diaphragms.

18. The device according to clam 16, wherein said means which is permeable to electromagnetic radiation has regions which are optically coupled with focusing optical elements through optical waveguides and/or integrated into said optical waveguides.

19. The device according to claim 16, wherein said substrate is a silicon wafer.

20. The device according to claim 16, wherein said detector is designed as a photodetector and disposed at the bottom of a channel traversing the substrate and the excitation radiation can in particular be irradiated at an angle of 0°<angle<180° with respect to the detector.

21. The device according to claim 16, characterized in that said detector is designed as a multidetector.

22. The device according to claim 16, characterized in that said substrate is a piezoelectric element.

23. The device according to claim 18, wherein said focusing optical elements are as microlenses, gradient index lenses or binary optical elements.

* * * * *